US012735715B2

(12) United States Patent
Park et al.

(10) Patent No.: US 12,735,715 B2
(45) Date of Patent: Sep. 15, 2026

(54) PROMOTER AND USE THEREOF

(71) Applicant: CJ CHEILJEDANG CORPORATION, Seoul (KR)

(72) Inventors: Goun Park, Seoul (KR); Sojung Park, Seoul (KR); Han Hyoung Lee, Seoul (KR); Woosung Choi, Seoul (KR); Heejung Kim, Seoul (KR); Jaemin Lee, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 459 days.

(21) Appl. No.: 18/560,239

(22) PCT Filed: Mar. 3, 2022

(86) PCT No.: PCT/KR2022/002984
§ 371 (c)(1),
(2) Date: Nov. 10, 2023

(87) PCT Pub. No.: WO2022/239942
PCT Pub. Date: Nov. 17, 2022

(65) Prior Publication Data

US 2024/0229049 A1 Jul. 11, 2024

(30) Foreign Application Priority Data

May 12, 2021 (KR) ........................ 10-2021-0061306

(51) Int. Cl.

| | |
|---|---|
| ***C12N 15/77*** | (2006.01) |
| ***C12N 9/06*** | (2006.01) |
| ***C12N 15/63*** | (2006.01) |
| ***C12P 13/06*** | (2006.01) |
| ***C12P 13/08*** | (2006.01) |
| ***C12R 1/15*** | (2006.01) |
| ***C40B 40/06*** | (2006.01) |

(52) U.S. Cl.
CPC ........... *C12N 15/77* (2013.01); *C12N 9/0016* (2013.01); *C12P 13/06* (2013.01); *C12P 13/08* (2013.01); *C12N 2800/60* (2013.01); *C12N 2830/34* (2013.01); *C12R 2001/15* (2021.05); *C12Y 104/01003* (2013.01)

(58) Field of Classification Search
None
See application file for complete search history.

(56) References Cited

U.S. PATENT DOCUMENTS

| | | | | |
|---|---|---|---|---|
| 8,110,672 | B2 | 2/2012 | Stephanopoulos et al. | |
| 8,637,295 | B1 | 1/2014 | Claes et al. | |
| 2009/0286290 | A1 | 11/2009 | Hara et al. | |
| 2023/0279366 | A1 * | 9/2023 | Sun ...................... | C12N 9/0016 435/107 |

FOREIGN PATENT DOCUMENTS

| | | | |
|---|---|---|---|
| JP | 2004-313202 | A | 11/2004 |
| JP | 2010-041920 | A | 2/2010 |
| KR | 10-2001-0032426 | A | 4/2001 |
| KR | 10-0924065 | B1 | 10/2009 |
| KR | 10-2016-0072278 | A | 6/2016 |
| KR | 10-1947959 | B1 | 2/2019 |
| KR | 10-2011994 | B1 | 8/2019 |
| KR | 10-1996769 | B1 | 10/2019 |
| KR | 10-2028554 | B1 | 10/2019 |
| KR | 10-2020-0136813 | A | 12/2020 |
| WO | 2008/013432 | A1 | 1/2008 |
| WO | 2022/017221 | A1 | 1/2022 |

OTHER PUBLICATIONS

International Search Report issued in corresponding International Patent Application No. PCT/KR2022/002984 dated Jun. 10, 2022.
Ishida et al., "Improvement of an I-Threonine Producer Derived from Brevibacterium flavum of *Escherichia coli* K-12", Agricultural and Biological Chemistry. vol. 53, Issue 8, (1989), pp. 2269-2271.
Van Der Rest et al., "A heat shock following electroporation induces highly efficient transformation of Corynebacterium glutamicum with xenogeneic plasmid DNA", Applied Microbiology and Biotechnology, vol. 52, No. 4, (1999), pp. 541-545.
Gory et al., "Use of green fuorescent protein to monitor Lactobacillus sakei in fermented meat products", FEMS Microbiology Letters, vol. 194, (2001). pp. 127-133.
Park et al., "Construction of heat-inducible expression vector of Corynebacterium glutamicum and C. ammoniagenes: fusion of lambda operator with promoters isolated from C. ammoniagenes.", Journal of Microbiology and Biotechnology, vol. 18, No. 4, (2008), pp. 639-647.
Office Action issued in corresponding Japanese Patent Application No. 2023-569978, dated Oct. 15, 2024.
Asakura et al., "Altered Metabolic Flux due to Deletion of odhA causes L-Glutamate Overproduction in Corynebacterium glutamicum", Applied and Environmental Microbiology, vol. 73, No. 4, Feb. 2007, pp. 1308-1319.
Hanszler et al., "A game with many players: Control of gdh transcription in Corynebacterium glutamicum", Journal of Biotechnology, vol. 142, 2009, pp. 114-122.
Extended European Search Report issued in corresponding European Patent Application No. 22807591.7, dated February 11, 2025.

* cited by examiner

*Primary Examiner* — Manjunath N Rao
*Assistant Examiner* — Jae W Lee
(74) *Attorney, Agent, or Firm* — Morgan, Lewis & Bockius LLP

(57) ABSTRACT

The present disclosure relates to relates to promoter variants and *Corynebacterium* mutant strain, and methods of use thereof.

21 Claims, No Drawings

Specification includes a Sequence Listing.

SEQUENCE LISTING

```
<160> NUMBER OF SEQ ID NOS: 28

<210> SEQ ID NO 1
<211> LENGTH: 330
<212> TYPE: DNA
<213> ORGANISM: Corynebacterium glutamicum

<400> SEQUENCE: 1

attctttgtg gtcatatctg tgcgacactg ccataattga acgtgagcat ttaccagcct      60

aaatgcccgc agtgagttaa gtctcaaagc aagaagttgc tctttagggc atccgtagtt     120

taaaactatt aaccgttagg tatgacaagc cggttgatgt gaacgcagtt tttaaaagtt     180

tcaggatcag atttttcaca ggcattttgc tccagcaaac gcctaggatg tacatggtgc     240
```

```
cctcaatggg aaccaccaac atcactaaat ggcccaggta cacactttaa aatcgtgcgc    300

gcatgcagcc gagatgggaa cgaggaaatc                                     330


<210> SEQ ID NO 2
<211> LENGTH: 330
<212> TYPE: DNA
<213> ORGANISM: Artificial Sequence
<220> FEATURE:
<223> OTHER INFORMATION: Pm3gdh

<400> SEQUENCE: 2

attctttgtg gtcatatctg tgcgactgtg gtatacttga acgtgagcat ttaccagcct     60

aaatgcccgc agtgagttaa gtctcaaagc aagaagttgc tctttagggc atccgtagtt    120

taaaactatt aaccgttagg tatgacaagc cggttgatgt gaacgcagtt tttaaaagtt    180

tcaggatcag atttttcaca ggcattttgc tccagcaaac gcctaggatg tacatggtgc    240

cctcaatggg aaccaccaac atcactaaat ggcccaggta cacactttaa aatcgtgcgc    300

gcatgcagcc gagatgggaa cgaggaaatc                                     330


<210> SEQ ID NO 3
<211> LENGTH: 330
<212> TYPE: DNA
<213> ORGANISM: Artificial Sequence
<220> FEATURE:
<223> OTHER INFORMATION: Pm16gdh

<400> SEQUENCE: 3

attctttgtg gtcatatctg tgcgactgtg gtatacttga acgtgagcat ttaccagcct     60

aaatgtccgc agtgagttaa gtctcaaagc aagaagttgc tctttagggc atccgtagtt    120

taaaactatt aaccgttagg tatgacaagc cggttgatgt gaacgcagtt tttaaaagtt    180

tcaggatcag atttttcaca ggcattttgc tccagcaaac gcctaggatg tacatggtgc    240

cctcaatggg aaccaccaac gtcactaaat ggcccaggta cacactttaa aatcgtgcgc    300

gcatgcagcc gagatgggaa cgaggaaatc                                     330


<210> SEQ ID NO 4
<211> LENGTH: 330
<212> TYPE: DNA
<213> ORGANISM: Artificial Sequence
<220> FEATURE:
<223> OTHER INFORMATION: Pm78gdh

<400> SEQUENCE: 4

attctttgtg gtcatatctg tgcgactgtg gtatacttga acgtgagcat ttaccagcct     60

aaatgtccgc agtgagttaa gtctcaaagc aagaagttgc tctttagggc atccgtagtt    120

taaaactatt aaccgttagg tatgacaagc cggttgatgt gaacgcagtt tttaaaagtt    180

tcaggatcag atttttcaca ggcattttgc tccagcaaac gcctaggatg tacatggtgc    240

cctcaatggg aaccaccaac atcactaaat ggcccaggta cacactttaa aatcgtgcgc    300

gcatgcagcc gagatgggaa cgaggaaatc                                     330


<210> SEQ ID NO 5
<211> LENGTH: 39
<212> TYPE: DNA
<213> ORGANISM: Artificial Sequence
<220> FEATURE:
<223> OTHER INFORMATION: Pgdhm primer

<400> SEQUENCE: 5
```

ctctagaact agtggatcca ttctttgtgg tcatatctg 39

<210> SEQ ID NO 6
<211> LENGTH: 40
<212> TYPE: DNA
<213> ORGANISM: Artificial Sequence
<220> FEATURE:
<223> OTHER INFORMATION: Pgdhm primer

<400> SEQUENCE: 6
agttcttctc ctttactcat gatttcctcg ttcccatctc 40

<210> SEQ ID NO 7
<211> LENGTH: 40
<212> TYPE: DNA
<213> ORGANISM: Artificial Sequence
<220> FEATURE:
<223> OTHER INFORMATION: GFP primer

<400> SEQUENCE: 7
gagatgggaa cgaggaaatc atgagtaaag gagaagaact 40

<210> SEQ ID NO 8
<211> LENGTH: 37
<212> TYPE: DNA
<213> ORGANISM: Artificial Sequence
<220> FEATURE:
<223> OTHER INFORMATION: GFP primer

<400> SEQUENCE: 8 ccccctcga ggtcgactta tttgtagagc tcatcca 37

<210> SEQ ID NO 9
<211> LENGTH: 20
<212> TYPE: DNA
<213> ORGANISM: Artificial Sequence
<220> FEATURE:
<223> OTHER INFORMATION: Pgdhm primer

<400> SEQUENCE: 9
attctttgtg gtcatatctg 20

<210> SEQ ID NO 10
<211> LENGTH: 20
<212> TYPE: DNA
<213> ORGANISM: Artificial Sequence
<220> FEATURE:
<223> OTHER INFORMATION: Pgdhm primer

<400> SEQUENCE: 10
gatttcctcg ttcccatctc 20

<210> SEQ ID NO 11
<211> LENGTH: 38
<212> TYPE: DNA
<213> ORGANISM: Artificial Sequence
<220> FEATURE:
<223> OTHER INFORMATION: pDZ-Pm3, 4, 6_gdh primer

<400> SEQUENCE: 11
gtgaattcga gctcggtacc ccgtcggtgg gggagttg 38

<210> SEQ ID NO 12
<211> LENGTH: 36
<212> TYPE: DNA

<213> ORGANISM: Artificial Sequence
<220> FEATURE:
<223> OTHER INFORMATION: pDZ-Pm3, 4, 6_gdh primer

<400> SEQUENCE: 12
gatatgacca caaagaatta aaattgtttg aaaatt 36

<210> SEQ ID NO 13
<211> LENGTH: 36
<212> TYPE: DNA
<213> ORGANISM: Artificial Sequence
<220> FEATURE:
<223> OTHER INFORMATION: pDZ-Pm3, 4, 6_gdh primer

<400> SEQUENCE: 13
aattttcaaa caattttaat tctttgtggt catatc 36

<210> SEQ ID NO 14
<211> LENGTH: 38
<212> TYPE: DNA
<213> ORGANISM: Artificial Sequence
<220> FEATURE:
<223> OTHER INFORMATION: pDZ-Pm3, 4, 6_gdh primer

<400> SEQUENCE: 14
cctgctcatc aactgtcatg atttcctcgt tcccatct 38

<210> SEQ ID NO 15
<211> LENGTH: 38
<212> TYPE: DNA
<213> ORGANISM: Artificial Sequence
<220> FEATURE:
<223> OTHER INFORMATION: pDZ-Pm3, 4, 6_gdh primer

<400> SEQUENCE: 15
agatgggaac gaggaaatca tgacagttga tgagcagg 38

<210> SEQ ID NO 16
<211> LENGTH: 39
<212> TYPE: DNA
<213> ORGANISM: Artificial Sequence
<220> FEATURE:
<223> OTHER INFORMATION: pDZ-Pm3, 4, 6_gdh primer

<400> SEQUENCE: 16
ggtcgactct agaggatccc ccaactccga tgtcacctg 39

<210> SEQ ID NO 17
<211> LENGTH: 41
<212> TYPE: DNA
<213> ORGANISM: Artificial Sequence
<220> FEATURE:
<223> OTHER INFORMATION: lysC(L377K) primer

<400> SEQUENCE: 17
gtgaattcga gctcggtacc ctccaagatt ttggtgctgc g 41

<210> SEQ ID NO 18
<211> LENGTH: 40
<212> TYPE: DNA
<213> ORGANISM: Artificial Sequence
<220> FEATURE:
<223> OTHER INFORMATION: lysC(L377K) primer

<400> SEQUENCE: 18
atctcagagg tggaaatctt ttcgatgttc acgttgacat 40

<210> SEQ ID NO 19
<211> LENGTH: 40
<212> TYPE: DNA
<213> ORGANISM: Artificial Sequence
<220> FEATURE:
<223> OTHER INFORMATION: lysC(L377K) primer

<400> SEQUENCE: 19
atgtcaacgt gaacatcgaa aagatttcca cctctgagat 40

<210> SEQ ID NO 20
<211> LENGTH: 41
<212> TYPE: DNA
<213> ORGANISM: Artificial Sequence
<220> FEATURE:
<223> OTHER INFORMATION: lysC(L377K) primer

<400> SEQUENCE: 20
ggtcgactct agaggatccc cgttcacctc agagacgatt a 41

<210> SEQ ID NO 21
<211> LENGTH: 41
<212> TYPE: DNA
<213> ORGANISM: Artificial Sequence
<220> FEATURE:
<223> OTHER INFORMATION: hom(R398Q) primer

<400> SEQUENCE: 21
gtgaattcga gctcggtacc ctttccacac ccgtgttacc g 41

<210> SEQ ID NO 22
<211> LENGTH: 40
<212> TYPE: DNA
<213> ORGANISM: Artificial Sequence
<220> FEATURE:
<223> OTHER INFORMATION: hom(R398Q) primer

<400> SEQUENCE: 22
atcatcgcgc tcttcctgtt ggattgtacg cagggagatt 40

<210> SEQ ID NO 23
<211> LENGTH: 40
<212> TYPE: DNA
<213> ORGANISM: Artificial Sequence
<220> FEATURE:
<223> OTHER INFORMATION: hom(R398Q) primer

<400> SEQUENCE: 23
aatctccctg cgtacaatcc aacaggaaga gcgcgatgat 40

<210> SEQ ID NO 24
<211> LENGTH: 41
<212> TYPE: DNA
<213> ORGANISM: Artificial Sequence
<220> FEATURE:
<223> OTHER INFORMATION: hom(R398Q) primer

<400> SEQUENCE: 24
ggtcgactct agaggatccc caaccattag ctgcagcaac a 41

<210> SEQ ID NO 25
<211> LENGTH: 20
<212> TYPE: DNA
<213> ORGANISM: Artificial Sequence
<220> FEATURE:

-continued

<223> OTHER INFORMATION: lysC(L377K) primer

<400> SEQUENCE: 25
tcctaatgca cagaagctgg 20

<210> SEQ ID NO 26
<211> LENGTH: 20
<212> TYPE: DNA
<213> ORGANISM: Artificial Sequence
<220> FEATURE:
<223> OTHER INFORMATION: lysC(L377K) primer

<400> SEQUENCE: 26
gtggtgcagt tagggttcgc 20

<210> SEQ ID NO 27
<211> LENGTH: 20
<212> TYPE: DNA
<213> ORGANISM: Artificial Sequence
<220> FEATURE:
<223> OTHER INFORMATION: hom(R398Q) primer

<400> SEQUENCE: 27
atccaactgc agacgtcgaa 20

<210> SEQ ID NO 28
<211> LENGTH: 20
<212> TYPE: DNA
<213> ORGANISM: Artificial Sequence
<220> FEATURE:
<223> OTHER INFORMATION: hom(R398Q) primer

<400> SEQUENCE: 28
atctgggtgg ccttcaaagg 20

PROMOTER AND USE THEREOF

A computer readable text file, entitled "133660-04-9019-US_Sequence_Listing_ST25.txt," created on or about Nov. 7, 2023, with a file size of 7,059 bytes contains the sequence listing for this application and is hereby incorporated by reference in its entirety.

TECHNICAL FIELD

The present disclosure relates to a novel promoter and a method for producing a target substance by using the same, and more specifically to a novel polynucleotide having promoter activity, a vector and a microorganism of the genus *Corynebacterium* including the same, a method for producing a target substance by using the microorganism, and use of the promoter.

BACKGROUND ART

A variety of studies on the production of target substances (e.g., amino acids) in microorganisms have been directed to eco-friendly and safe production methods, among which studies for producing target substances in large quantities in microorganisms of the genus *Corynebacterium* have been continuously conducted. A microorganism of the genus *Corynebacterium* (*Corynebacterium* sp.), especially *Corynebacterium glutamicum*, is a gram-positive microorganism that is often used to produce L-amino acids and other useful substances. For the production of L-amino acids and other useful substances, various studies have been conducted to develop microorganisms enabling high-efficiency production and fermentation process technology.

L-Lysine, a representative substance produced by microorganisms of the genus *Corynebacterium*, is used for industries of animal feeds and human pharmaceuticals and cosmetics and produced by fermentation using *Corynebacterium* strains. Microorganisms with enhanced L-lysine biosynthesis-related genes and L-lysine production methods using the same are known (KR 10-0924065 B1).

L-Threonine, which is a kind of essential amino acid, is widely used as a feed and food additive and is also used, for the purpose of medicines, as a synthetic raw material of infusions and pharmaceuticals. Since animals with a vegetarian diet are prone to lacking L-threonine due to less L-threonine in vegetable proteins, L-threonine is especially usefully used as an additive for animal feed. L-Threonine is mainly produced by fermentation using *E. coli* or *Corynebacterium* microorganisms developed by artificial mutation or genetic recombination. Typically, a method using a recombinant strain wherein L-threonine is produced by introducing *E. coli*-derived threonine operon into the threonine-producing strain *Brevibacterium flavum* (TURBA E, et al., *Agric. Biol. Chem.* 53:2269-2271, 1989) is known.

O-Acetyl-homoserine is a substance used as a precursor for the production of methionine and is an intermediate in the biosynthesis pathway of methionine (WO 2008/013432). O-Acetyl-L-homoserine is synthesized from L-homoserine and acetyl-CoA as substrates by homoserine O-acetyl transferase.

Isoleucine, which is an essential amino acid that is not synthesized in the body, is known to have effects of growth promotion, nerve function enhancement, liver function enhancement, and muscle strengthening, and is usually produced by fermentation using microorganisms.

There is still a need for the development of a universal promoter since a system showing high expression efficiencies in various microorganisms, that is, microorganisms of the genus *Escherichia*, microorganisms of the genus *Corynebacterium*, or microorganisms of the genus *Bacillus*, is required. It is also expected that a universal promoter, when developed without limitation to a specific target substance, can be utilized in the production of various substances.

DISCLOSURE

Technical Problem

It was identified in the present disclosure that a novel synthetic promoter, when present in a forward direction, has high expression activity with respect to downstream genes, compared with a known promoter, leading to the production of various target substances.

Technical Solution

An aspect of the present disclosure is to provide a polynucleotide having promoter activity.

Another aspect of the present disclosure is to provide a vector or an expression cassette including: the polynucleotide; and a gene encoding a target protein and operably linked to the polynucleotide.

Still another aspect of the present disclosure is to provide a microorganism of the gene *Corynebacterium*, including: the polynucleotide; or the polynucleotide and a gene encoding a target protein and operably linked to the polynucleotide.

Still another aspect of the present disclosure is to provide a method for producing a target substance, the method including: culturing the microorganisms of the genus *Corynebacterium* in a medium; and recovering a target substance in the medium.

Still another aspect of the present disclosure is to provide use of a polynucleotide as a promoter, the polynucleotide having promoter activity, in which the nucleotides at positions 27, 28, 31, 32, and 36 are substituted with other nucleotides in the polynucleotide sequence of SEQ ID NO: 1.

Advantageous Effects

The novel polynucleotide having promoter activity of the present disclosure can be introduced into a microorganism producing a target substance, thereby increasing the production of the target substance. Due to the improved production yields, the convenience of production, the reduction in manufacturing costs, and other effects can be expected in terms of an industrial aspect.

DETAILED DESCRIPTION OF THE INVENTION

The present disclosure will be specifically described as follows. Each description and embodiment disclosed in this disclosure may also be applied to other descriptions and embodiments. That is, all combinations of various elements disclosed in this disclosure fall within the scope of the present disclosure. Furthermore, the scope of the present disclosure is not limited by the specific description below.

Further, a person skilled in the art will recognize, or be able to ascertain, by using no more than routine experimentation, many equivalents to the specific embodiments of the disclosure described herein. Such equivalents are intended to be encompassed by the present disclosure.

An aspect of the present disclosure is to provide a polynucleotide having promoter activity.

Specifically, the polynucleotide having promoter activity of the present disclosure may be a polynucleotide having promoter activity and including at least one polynucleotide substitution in the polynucleotide sequence of SEQ ID NO: 1.

As used herein, the term "polynucleotide" refers to a nucleotide polymer composed of nucleotide monomers covalently linked in a long chain, and the polynucleotide is a DNA strand having a predetermined length or longer.

As used herein, the term "polynucleotide having promoter activity" refers to a DNA region present in the vicinity of a site where a gene to be expressed, that is, a target gene is transcribed, including a site to which RNA polymerase, an enhancer, or the like binds for the expression of the target gene.

The polynucleotide having promoter activity of the present disclosure may be used as a universal enhancing promoter. For example, the polynucleotide may be used as a promoter capable of enhancing the expression of a polypeptide having glutamate dehydrogenase (gdh) activity. Alternatively, the polynucleotide may be a polynucleotide that is involved in increasing the production or yield of a target substance, specifically lysine, threonine, O-acetyl homoserine, or isoleucine.

The polynucleotide of the present disclosure may include any polynucleotide having promoter activity without limitation. Specifically, the polynucleotide having promoter activity of the present disclosure may be a polynucleotide having promoter activity and including at least one, at least two, at least three, at least four, at least five, at least six, or at least seven nucleotide substitutions in the polynucleotide sequence of SEQ ID NO: 1.

An example of the polynucleotide sequence of SEQ ID NO: 1 may be a polynucleotide having promoter activity of glutamate dehydrogenase. A polynucleotide having a substitution of a particular nucleotide in the polynucleotide sequence of SEQ ID NO: 1 as long as having promoter activity may also be a polynucleotide having promoter activity of glutamate dehydrogenase. The polynucleotide sequence of SEQ ID NO: 1 may be a representative polynucleotide sequence for indicating mutation positions, and other polynucleotide sequences corresponding thereto and having promoter activity are also included in the sequence into which mutations can be introduced. For example, any polynucleotide sequence that can serve as a promoter of a polypeptide having activity of glutamate dehydrogenase (gdh) or activity corresponding thereto may be included in the range of a sequence to which the mutations of the present disclosure can be introduced, without limitation.

The nucleotide sequence of SEQ ID NO: 1 can be confirmed in NCBI GenBank, a known database, and the sequence corresponding to SEQ ID NO: 1 as a sequence capable of serving as a promoter of glutamate dehydrogenase may be derived from *Corynebacterium* sp., specifically *Corynebacterium glutamicum*. However, sequences having activity equivalent to or higher than that of the polynucleotide may be included in the promoter of the present disclosure without limitation.

The polynucleotide having promoter activity provided in the present disclosure may be a polynucleotide, of which promoter activity is enhanced by a substitution of a nucleotide at a specific position in the existing polynucleotide sequence having the promoter activity.

In an embodiment, the polynucleotide having promoter activity of the present disclosure may include a polynucleotide having promoter activity in which at least one nucleotide is substituted with another nucleotide in the nucleotide sequence of SEQ ID NO: 1. Specifically, the polynucleotide of the present disclosure may be composed of a polynucleotide having promoter activity in which at least one nucleotide is substituted with another nucleotide in the nucleotide sequence of SEQ ID NO: 1. The polynucleotide having promoter activity may be used interchangeably with "modified promoter" herein.

In an embodiment, the modified promoter may be a polynucleotide having promoter activity and including a substitution of at least one nucleotide selected from the group consisting of the nucleotides at positions 27, 28, 31, 32, and 36 with another nucleotide in SEQ ID NO: 1. Specifically, the modified promoter may be a promoter having substitutions with other nucleotides at least one, at least two, at least three, at least four, or all the five positions among the above-described positions or at positions corresponding thereto. In addition, the modified promoter may further have an additional substitution of a nucleotide at position 66 and/or 261.

The "another nucleotide" or "other nucleotides" are not limited as long as the nucleotide or nucleotides are different from the nucleotide or nucleotides before substitution. Taking the example, adenine (A) as the nucleotide at position 27 in SEQ ID NO: 1, the wording "the nucleotide at position 27 was substituted with another nucleotide in SEQ ID NO: 1" means a substitution with cytosine (C), thymine (T), or guanine (G) except for adenine. Unless indicated otherwise, the wording that a certain nucleotide was "substituted" in the present disclosure means a substitution with a nucleotide different from the nucleotide before substitution.

Meanwhile, a person skilled in the art can grasp nucleotides at positions, corresponding to the nucleotides at positions 27, 28, 31, 32, 36, 66, and 261 in SEQ ID NO: 1 of the present disclosure, in any polynucleotide sequence through sequence alignment known in the art, and even if not separately described herein, the wording "nucleotide at a particular position in a particular sequence number" obviously means including even "a nucleotide at a position corresponding" thereto in any polynucleotide sequence. Therefore, any polynucleotide sequence having promoter activity, in which any one or more nucleotides selected from the group consisting of nucleotides at positions corresponding to positions 27, 28, 31, 32, 36, 66, and 261 are substituted with other nucleotides in the polynucleotide sequence of SEQ ID NO: 1 is also included in the scope of the present disclosure.

In an embodiment, the polynucleotide having promoter activity of the present disclosure may be a polynucleotide in which any one or more nucleotides selected from the group consisting of the nucleotides at positions 27, 28, 31, 32, 36, 66, and 261 are substituted with other nucleotides in the polynucleotide sequence of SEQ ID NO: 1.

Specifically, the polynucleotide having promoter activity of the present disclosure may be a polynucleotide in which in the polynucleotide sequence of SEQ ID NO: 1, the nucleotides at positions 27, 28, 31, 32, and 36 are substituted with other nucleotides; the nucleotides at positions 27, 28, 31, 32, 36, 66, and 261 are substituted with other nucleotides; and the nucleotides at positions 27, 28, 31, 32, 36, and 66 are substituted with other nucleotides, but is not limited thereto.

For example, a promotor having higher activity than a non-substituted (non-modified) promoter sequence can be provided when at least one, at least two, at least three, at least four, at least five, at least six, or at least seven nucleotides among the positions corresponding to positions 27, 28, 31, 32, 36, 66, and 261 in the polynucleotide of SEQ ID NO: 1 are substituted with other nucleotides. Specifically, the polynucleotide having promoter activity of the present disclosure may be a polynucleotide in which the nucleotides at positions 27, 28, 31, 32, and 36 are substituted with other nucleotides in the polynucleotide sequence of SEQ ID NO: 1. The polynucleotide of the present disclosure may also be a polynucleotide having promoter activity in which the nucleotides at positions 66 and 261 are further substituted with other nucleotides or the nucleotide at position 66 is substituted with another nucleotide.

As a specific example, the polynucleotide having promoter activity of the present disclosure may be a polynucleotide in which in the polynucleotide sequence of SEQ ID NO: 1, the nucleotide adenine (A) at position 27 is substituted with thymine (T), the nucleotide cytosine (C) at position 28 is substituted with guanine (G), the nucleotide cytosine (C) at position 31 is substituted with guanine (G), the nucleotide cytosine (C) at position 32 is substituted with thymine (T), and the nucleotide adenine (A) at position 36 is substituted with cytosine (C); in the polynucleotide sequence of SEQ ID NO: 1, the nucleotide adenine (A) at position 27 is substituted with thymine (T), the nucleotide cytosine (C) at position 28 is substituted with guanine (G), the nucleotide cytosine (C) at position 31 is substituted with guanine (G), the nucleotide cytosine (C) at position 32 is substituted with thymine (T), the nucleotide adenine (A) at position 36 is substituted with cytosine (C), the nucleotide cytosine (C) at position 66 is substituted with thymine (T), and the nucleotide adenine (A) at position 261 is substituted with guanine (G); and in the polynucleotide sequence of SEQ ID NO: 1, the nucleotide adenine (A) at position 27 is substituted with thymine (T), the nucleotide cytosine (C) at position 28 is substituted with guanine (G), the nucleotide cytosine (C) at position 31 is substituted with guanine (G), the nucleotide cytosine (C) at position 32 is substituted with thymine (T), the nucleotide adenine (A) at position 36 is substituted with cytosine (C), and the nucleotide cytosine (C) at position 66 is substituted with thymine (T).

As a more specific example, the polynucleotide of the present disclosure may be a polynucleotide set forth in a polynucleotide sequence of any one of SEQ ID NOS: 2 to 4. Specifically, the polynucleotide having promoter activity of the present disclosure may contain or (essentially) consist of the polynucleotide sequence of SEQ ID NO: 2, 3, or 4.

Without being limited to the above-described embodiments, various modifications to the polynucleotide sequence may also be included within the range that does not significantly reduce promoter activity.

The polynucleotide having promoter activity of the present disclosure may be a polynucleotide sequence having at least 70%, 80%, 85%, 90%, 95%, 96%, 97%, 98%, or 99% homology or identity with SEQ ID NO: 2, 3, or 4. The nucleotide sequences having homology or identity may exclude the sequence having 100% identity from the above range or may be sequences having identity of less than 100%.

Although described as "polynucleotide having a nucleotide sequence set forth in a particular sequence number" or "polynucleotide containing a nucleotide sequence set forth in a particular sequence number" herein, a polynucleotide having a polynucleotide sequence, a part of which is deleted, modified, substituted, or added, may also be obviously used in the present disclosure as long as the polynucleotide has the same or corresponding activity to the polypeptide consisting of the nucleotide sequence of the corresponding sequence number.

For example, when having the same or corresponding activity to the polynucleotide, a polynucleotide in which a nonsense sequence is added to the inside or the end of the nucleotide sequence of the corresponding sequence number or a part of the sequence of the inside or the end of the nucleotide sequence of the corresponding sequence number is deleted is also included in the scope of the present disclosure.

The homology or identity refers to a degree of relevance between two given nucleotide sequences and may be expressed as a percentage.

The terms homology and identity may be often used interchangeably.

The sequence homology or identity of conserved polynucleotides may be determined by a standard alignment algorithm, and default gap penalties established by a program to be used may be used together. Substantially, homologous or identical sequences may generally hybridize with each other along the entire sequences or at least about 50%, 60%, 70%, 80%, or 90% of the full-lengths of the sequences under moderate or highly stringent conditions. In hybridization, polynucleotides containing a degenerate codon instead of a codon are also considered.

Whether any two polynucleotide sequences have homology, similarity, or identity may be determined using a known computer algorithm, such as "FASTA" program, by using default parameters as in, for example, Pearson et al. (1988) *Proc. Natl. Acad. Sci. USA* 85:2444. Alternatively, this may be determined using the Needleman-Wunsch algorithm (Needleman and Wunsch, 1970, *J. Mol. Biol.* 48:443-453), which is performed in the Needleman program of the European Molecular Biology Open Software Suite (EMBOSS) package (Rice et al., 2000, *Trends Genet.* 16:276-277) (version 5.0.0 or later) (including GCG program package (Devereux, J., et al., *Nucleic Acids Research* 12:387 (1984)), BLASTP, BLASTN, FASTA (Atschul, S. F. et al., *J MOLEC BIOL* 215:403 (1990); *Guide to Huge Computers*, Martin J. Bishop, ed., Academic Press, San Diego, 1994, and CARILLO et al. (1988) *SIAM J Applied Math* 48:1073). For example, the homology, similarity, or identity may be determined using BLAST or ClustalW from the National Center for Biotechnology Information database.

The homology, similarity, or identity of polynucleotides may be determined by comparing sequence information through the GAP computer program, for example, Needleman et al., (1970), *J Mol Biol.* 48:443, as disclosed in Smith and Waterman, *Adv. Appl. Math* (1981) 2:482. Briefly, the GAP program defines the homology, similarity, or identity as the value obtained by dividing the number of similarly aligned symbols (i.e., nucleotides or amino acids) by the total number of the symbols in the shorter of the two sequences. The default parameters for the GAP program may include: (1) a binary comparison matrix (containing a value of 1 for identity and a value of 0 for non-identity) and the weighted comparison matrix of Gribskov et al. (1986) *Nucl. Acids Res.* 14:6745 as disclosed in Schwartz and Dayhoff, eds., *Atlas of Protein Sequence and Structure*, National Biomedical Research Foundation, pp. 353-358 (1979) (or EDNAFULL (EMBOSS version of NCBI NUC4.4) substitution matrix); (2) a penalty of 3.0 for each gap and an additional 0.10 penalty for each symbol in each gap (or a gap open penalty of 10 and a gap extension penalty of 0.5); and (3) no penalty for end gaps. Therefore, the term "homology" or "identity" used herein refers to the relatedness between sequences.

In addition, any polynucleotide sequence that can hybridize with a probe capable of being prepared from a known gene, for example, a complementary sequence to a part or the entirety of the above-described polynucleotide sequence, under stringent conditions and has the same activity may be included without limitation. The term "stringent conditions" refers to conditions that enable specific hybridization between polynucleotides. These conditions are specifically described in the literature (e.g., J. Sambrook et al., *Molecular Cloning, A Laboratory Manual,* 2nd Edition, Cold Spring Harbor Laboratory press, Cold Spring Harbor, New York, 1989; F. M. Ausubel et al., *Current Protocols in Molecular Biology*, John Wiley & Sons, Inc., New York). For example, the conditions may include conditions under which genes having high homology or identity, such as, genes having at least 40%, specifically at least 70%, at least 80%, at least 85%, or at least 90%, more specifically at least 95%, still more specifically at least 97%, and even still more specifically at least 99% homology or identity hybridize with each other but genes having lower homology or identity than the above ranges do not hybridize with each other; or typical washing conditions for southern hybridization, i.e., washing is conducted once, specifically twice or three times at a salt concentration and temperature corresponding to 60° C., 1×SSC, and 0.1% SDS, specifically 60° C., 0.1×SSC, and 0.1% SDS, and more specifically 68° C., 0.1×SSC, and 0.1% SDS.

Hybridization requires that two nucleic acids have complementary sequences, although mismatches between bases may be possible depending on hybridization stringency. The term "complementary" is used to describe the relationship between nucleotide bases that can hybridize with each another. For example, as for DNA, adenine is complementary to thymine and cytosine is complementary to guanine. Therefore, the present disclosure may include not only substantially similar nucleic acid sequences but also isolated nucleic acid fragments complementary to the entire sequence.

Specifically, polynucleotides having homology or identity can be detected using hybridization conditions including a hybridization step at a $T_m$ value of 55° C. under the above-described conditions. In addition, the $T_m$ value may be 60° C., 63° C., or 65° C., but is not limited thereto, and may be appropriately adjusted by a person skilled in the art according to the purpose.

The appropriate stringency for hybridizing polynucleotides depends on the length of the polynucleotides and the degree of complementarity thereof, and variables thereof are well known in the art (see Sambrook et al., supra, 9.50-9.51 and 11.7-11.8).

The polynucleotide having promoter activity of the present disclosure may be used as a promoter.

The promoter may be located at the 5'-region of the initiation site of the transcription into mRNA.

The promoter of the present disclosure may have promoter activity enhanced compared with conventional promoters. That is, the promoter can increase the expression of a target gene as well as the expression and/or activity of a protein encoded by the target gene. For the purposes of the present disclosure, a target gene for expression enhancement may be changed depending on a product to be produced, and the promoter may be used as a universal promoter for enhancement of a target gene.

The term "target gene", for the purposes of the present disclosure, refers to a gene, of which the expression is regulated by the promoter sequence of the present disclosure. The protein encoded by the target gene may be expressed as "target protein", and the gene encoding the "target protein" may be expressed as a "target gene".

The polynucleotide encoding the target protein may have various modifications in the coding region thereof within the scope in which the polynucleotide sequence is not changed, due to codon degeneracy or in consideration of the codons preferred by an organism in which the polynucleotide is to be expressed. The polynucleotide sequence is as described above.

In an embodiment, the target protein may be a polypeptide having glutamate dehydrogenase (gdh) activity. That is, the target gene of the promoter may be a gene encoding a polypeptide having glutamate dehydrogenase (gdh) activity.

As used herein, the term "glutamate dehydrogenase (gdh)" may also be referred to as "glutamate dehydrogenase" or the like. The glutamate dehydrogenase is involved in the metabolism of glutamate to 2-oxoglutarate, and can produce an effect of improving the productivity of useful substances, such as lysine, threonine, O-acetyl homoserine, and isoleucine, through activity control thereof.

Examples of the gene encoding glutamate dehydrogenase may be gdh gene (NCgl1999) of *Corynebacterium glutamicum* ATCC13032 and the like, but is not limited thereto. A person skilled in the art can easily obtain information of genes encoding glutamate dehydrogenase from a known database (GenBank or the like).

Amino acid sequences constituting the glutamate dehydrogenase may be available in NCBI GenBank, a known database. For example, the amino acid sequence may be derived from *Corynebacterium glutamicum.*

In addition, the "polypeptide having glutamate dehydrogenase activity" of the present disclosure includes not only a wild type, non-modified type, or native type of glutamate dehydrogenase, but also a variant having the same or enhanced activity with respect thereto.

As used herein, the term "modified polypeptide", which has the same meaning as "variant", refers to a protein, in which at least one amino acid in the conservative substitution and/or modification is different from that of the recited sequence but of which the functions or properties are maintained.

A variant differs from an identified sequence by several amino acid substitutions, deletions, or additions. Such a variant can be usually identified by modifying one or more amino acids in the amino acid sequence of the protein and by evaluating the properties of the modified protein. That is, the ability of a variant may be increased compared with that of its native protein. In addition, some variants may include variants in which at least one part, such as an N-terminal leader sequence or a transmembrane domain, is removed.

The term "variant" may also be used interchangeably with "modification", "modified protein", "modified polypeptide", "mutant", "mutein", "divergent", "variant", or the like, and any term that is used in a sense of being mutated can be used without limitation thereto. For the purpose of the present disclosure, the variant may refer to those in which the activity of a mutated protein is increased compared with that of a native wild-type or non-modified protein, but the variant is not limited thereto.

As used herein, the term "conservative substitution" refers to substitution of one amino acid with another amino acid that has similar structural and/or chemical properties. The variant may have, for example, one or more conservative substitutions while still retaining one or more biological activities. Such amino acid substitutions may generally occur on the basis of similarities in polarity, charge, solubility, hydrophobicity, hydrophilicity, and/or amphipathic nature of residues.

In addition, a variant may include deletions or additions of amino acids that have a minimal effect on the characteristics and secondary structure of a polypeptide. For example, a polypeptide may be conjugated to a signal (or leader) sequence at the N-terminus of a protein, which co-translationally or post-translationally directs transfer of the protein. In addition, the polypeptide may also be conjugated to another sequence or a linker for identification, purification, or synthesis of the polypeptide.

The gene encoding the polypeptide having glutamate dehydrogenase of the present disclosure may be called "gdh gene".

The gene may be derived from the genus *Corynebacterium*, specifically *Corynebacterium glutamicum.*

In the present disclosure, "gdh gene", that is, the polynucleotide encoding the polypeptide having glutamate dehydrogenase activity may be variously modified in a coding region thereof within the range in which the amino acid sequence of the polypeptide is not changed, due to codon degeneracy or considering codons preferred by an organism in which the polypeptide is to be expressed.

The polypeptide having glutamate dehydrogenase of the present disclosure also includes a variant sequence, and specifically a protein variant that is modified to show enhanced activity of glutamate dehydrogenase.

In accordance with another aspect of the present disclosure, there is provided a composition for gene expression, the composition containing the polynucleotide having promoter activity of the present disclosure.

The composition for gene expression refers to a composition capable of expressing a gene that can be expressed by the polynucleotide having promoter activity of the present disclosure.

For example, the composition for gene expression may include the polynucleotide having promoter activity of the present disclosure, and may further include, without limitation, a configuration capable of operating the polynucleotide as a promoter.

In the composition for gene expression of the present disclosure, the polynucleotide may be in a form that is included in a vector so as to express a gene operably linked in a host cell into which the polynucleotide is introduced.

In accordance with another aspect of the present disclosure, there is provided an expression cassette including the polynucleotide having promoter activity, or the polynucleotide and a genes encoding a target protein.

As used herein, the term "expression cassette" refers to a unit cassette which includes the polynucleotide having promoter activity and a gene encoding a target protein and thus can express a target gene operably linked downstream of the promoter. Specifically, in the expression cassette, the polynucleotide having promoter activity may be operably linked to a gene encoding a target protein. As used herein, the term "operably linked" refers to a functional linkage between the gene sequence and the polynucleotide having promoter activity to initiate and mediate the transcription of a gene encoding a target protein.

Various factors that can help efficient expression of the target gene may be additionally included inside or outside such a gene expression cassette. The expression cassette may usually include a transcription termination signal, a ribosome binding site, and a translation terminal signal, in addition to the promoter operably linked to the target gene.

In an embodiment, the target protein may be a polypeptide having activity of glutamate dehydrogenase.

In accordance with another aspect of the present disclosure, there is provided a vector including the polynucleotide having promoter activity, or the polynucleotide and a gene encoding a target protein.

In an embodiment, the target protein may be a polypeptide having activity of glutamate dehydrogenase.

As used herein, the term "vector" refers to a DNA construct containing a polynucleotide sequence encoding the target protein, which is operably linked to an appropriate control sequence to express a target protein in a suitable host.

For the purposes of the present disclosure, the control sequence may include the polynucleotide having promoter activity of the present disclosure.

The control sequence may include a promoter capable of initiating transcription, any operator sequence for controlling such transcription, a sequence encoding an appropriate mRNA ribosomal binding site, and sequences for controlling the termination of transcription and translation. The vector, after transformation into an appropriate host cell, can replicate or function independently of the genome of the host, or may be integrated into the genome itself.

The vector used in the present disclosure is not particularly limited as long as expression can be made in a host cell, and the host cell can be transformed using any vector known in the art. Examples of the vector commonly used may include native or recombinant plasmids, cosmids, viruses, and bacteriophages.

For example, pWE15, M13, λLB3, λBL4, λIXII, λASHII, λAPII, λt10, λt11, Charon4A, and Charon21A may be used as phage vectors or cosmid vectors, and pBR-based, pUC-based, pBluescriptII-based, pGEM-based, pTZ-based, pCL-based, and pET-based vectors may be used as plasmid vectors.

In addition, an endogenous promoter in a chromosome can be replaced with the polynucleotide having promoter activity of the present disclosure through a vector for chromosome insertion in a host cell. For example, pECCG117, pDZ, pACYC177, pACYC184, pCL, pUC19, pBR322, pMW118, pCC1BAC, pCES208, or pXMJ19 vector may be used but are not limited thereto. Alternatively, a vector as a known technique may be used (Korean Patent No. 10-09240675).

The insertion of the polynucleotide into the chromosome may be performed using any method known in the art, for example, homologous recombination, but is not limited thereto. The vector may further include a selection maker for investigating the insertion or non-insertion of the chromosome. A selection marker is used for selection of cells transformed with the vector, that is, to investigate the insertion or non-insertion of a target nucleic acid molecule, and markers conferring selectable phenotypes, such as drug resistance, auxotrophy, resistance to cytotoxic drugs, and expression of surface proteins, may be used. Under the circumstances of the treatment with a selective agent, only the cells expressing the selection markers can survive or express other phenotypic traits, and thus the transformed cells can be selected. For example, a wild-type polynucleotide can be replaced with a modified polynucleotide through a vector for chromosomal insertion in a cell.

As used herein, the term "transformation" may indicate that a vector including a polynucleotide encoding a target protein is introduced into a host cell to allow the target protein to be expressed in the host cell.

The transformed polynucleotide may include any polypeptide that can be expressed in a host cell, regardless of whether the polypeptide is inserted and located into the chromosome of a host cell or located outside of the chromosome. In addition, the polynucleotide encoding the target protein may contain DNA and RNA encoding the target protein. The polynucleotide can be introduced in any form as long as the polynucleotide can be introduced and expressed in a host cell. For example, the polynucleotide encoding the target protein may be introduced, into the host cell, in the form of an expression cassette, which is a gene construct containing all the elements required for self-expression.

The expression cassette may usually include a promoter operably linked to the polynucleotide encoding the target protein, a transcription termination signal, a ribosome binding site, and a translation terminal signal. In addition, the polynucleotide having the target protein may be introduced in the form as it is into the host cell and operably linked to a sequence required for expression in the host cell, but is not limited thereto.

In addition, the term "operably linked" refers to a functional linkage between the gene sequence and a promoter sequence initiating and mediating the transcription of the polynucleotide encoding the target protein of the present disclosure.

For the purposes of the present disclosure, the promoter may be a polynucleotide having promoter activity of the present disclosure.

A method of transformation of the vector of the present disclosure includes any method of introducing a nucleic acid into a cell, and may be carried out by selecting a suitable standard technique known in the art according to the host cell. Examples of the method may include electroporation, calcium phosphate (CaPO4) precipitation, calcium chloride ($CaCl_2$) precipitation, retroviral infection, microinjection, a polyethyleneglycol (PEG) method, a DEAE-dextran method, a cationic liposome method, a lithium acetate-DMSO method, and the like, but are not limited thereto.

In accordance with another aspect of the present disclosure, there is provided a microorganism including: the polynucleotide having promoter activity of the present disclosure; an expression cassette including the polynucleotide and a gene encoding a target protein; or a vector including the polynucleotide and a gene encoding a target protein.

As used herein, the term "microorganism" encompasses all of wild-type microorganisms, or microorganisms with a naturally or artificially genetic modification, and refers to a microorganism in which a particular mechanism is attenuated or enhanced due to the insertion of an exogenous gene or the enhancement or attenuation of activity of an endogenous gene. Specifically, the microorganism may include: the polynucleotide having promoter activity of the present disclosure; and a target protein.

The target protein may be a polypeptide having activity of glutamate dehydrogenase (gdh). The polynucleotide having promoter activity of the present disclosure, the target protein, the polypeptide having activity of glutamate dehydrogenase (gdh), the vector, and the expression cassette are as described above.

The microorganism may be a microorganisms of the genus *Corynebacterium*, and specifically *Corynebacterium glutamicum*.

The microorganism may be a microorganism expressing glutamate dehydrogenase, a microorganism expressing a polypeptide having activity of glutamate dehydrogenase, or a microorganism into which a polypeptide having activity of glutamate dehydrogenase is introduced, but is not limited thereto.

In the present disclosure, the microorganism may include the polynucleotide having promoter activity of the present disclosure, and specifically may include the polynucleotide and/or a gene operably linked to the polynucleotide and encoding a target protein. Alternatively, the microorganism may include a vector or expression cassette including the polynucleotide or a gene expression control sequence and a gene encoding a target protein, but is not limited thereto. In addition, the polynucleotide, the gene encoding the target protein, the vector, and the expression cassette may be introduced into the microorganism by transformation, but is not limited thereto. Furthermore, as long as the gene can be expressed in the microorganism, it does not matter whether the polynucleotide and the gene encoding the target protein are located on the chromosome or outside of the chromosome.

As used herein, the term "to be expressed/is expressed" with respect to a protein refers to a state in which, for example, glutamate dehydrogenase or a variant thereof is introduced into a microorganism or is modified to be expressed in a microorganism. When the target protein is a protein present in a microorganism, the term refers to a state in which the activity of the protein is enhanced compared with the endogenous activity or the activity before modification of the protein.

Specifically, the term "introduction of a protein" may indicate that a microorganism exhibits activity of a particular protein which was not originally possessed thereby, or exhibits enhanced activity compared with the endogenous activity of the corresponding protein or the activity before modification thereof. For example, the term may indicate that a polynucleotide encoding a particular protein is introduced into the chromosome of a microorganism or a vector or expression cassette including a polynucleotide encoding a particular protein is introduced into a microorganism to exhibit the activity of the protein.

The term "enhancement of activity" may indicate that the activity of a particular protein possessed by a microorganism is enhanced compared with the endogenous activity or the activity before modification. The term "endogenous activity" may refer to the activity of a particular protein, originally possessed by a parental strain before transformation when a microorganism is transformed by genetic mutation caused by natural or artificial factors.

For the purpose of the present disclosure, the enhancement of activity may be attained by using the polynucleotide sequence having promoter activity of the present disclosure as an expression control sequence of a target protein. Since the target protein may be in a native form or a variant form as described above, the expression control sequence may be an expression control sequence of a gene encoding a variant protein or an expression control sequence of a gene encoding a native protein on the chromosome.

Besides, other activity enhancement methods may also be used in combination. For example, in addition to using the polynucleotide sequence having promoter activity of the present disclosure as an expression control sequence of a target protein, at least one method selected from the group consisting of: a method of increasing the intracellular copy number of a gene encoding a target protein, a method of replacing a gene encoding a native protein on the chromosome with a gene encoding the protein variant, and a method of additionally introducing a mutation into the gene encoding the protein so as to enhance the activity of the protein variant, and a method of introducing a protein variant into a microorganism, but is not limited thereto.

The activity of a target protein can be enhanced by using the polynucleotide having promoter activity of the present disclosure for expression control of the target protein in microorganisms.

For example, the activity or concentration of the corresponding protein may be increases by at least 1%, at least 10%, at least 25%, at least 50%, at least 75%, at least 100%, at least 150%, at least 200%, at least 300%, at least 400%, or at least 500%, and up to 1,000% or 2,000%, relative to the activity or concentration of a protein in a wild-type or un-modified microorganism strain, but is not limited thereto.

As used herein, the term "non-modified microorganism" does not exclude a strain including a mutation that may naturally occur in the microorganism, and refers to a native strain itself, a microorganism not including the polynucleotide having promoter activity of the present disclosure, or a microorganism not transformed with a vector including the polynucleotide having promoter activity of the present disclosure.

As used herein the term "microorganism producing a target substance" includes all of microorganisms with naturally or artificially occurring genetic modifications, and may refer to a microorganism in which a particular mechanism is attenuated or enhanced due to the insertion of an exogenous gene or the activity enhancement or inactivation of an endogenous gene, wherein the microorganism has genetic mutation or enhanced activity for the production of a target substance. For the purpose of the present disclosure, the microorganism producing the target substance may refer to a microorganism capable of producing the target substance in excess compared with a wild-type or non-modified microorganism by including the polynucleotide having promoter activity of the present disclosure.

The term "microorganism producing target substance" may be used interchangeably with the terms, such as "target substance-producing microorganism", "microorganism having target substance producing ability", "target substance-producing strain", "strain having target substance producing ability", and the like.

The target substance may be an amino acid, specifically lysine, threonine, O-acetyl homoserine, or isoleucine. As a more specific example, the lysine may be L-lysine, the threonine may be L-threonine, and the isoleucine may be L-isoleucine, but are not limited thereto.

For the purpose of the present disclosure, the microorganism producing the target substance may have an improvement in the ability to produce a target substance, specifically lysine, threonine, O-acetyl homoserine, or isoleucine.

Meanwhile, the target substance-producing microorganism may be a wild-type microorganism or a recombinant microorganism. The recombinant microorganism is as described above. The microorganism may further include a mutation, such as enhancing biosynthesis pathways for increasing target substance producing ability, releasing feedback inhibition, or inactivating genes attenuating degradation pathways or biosynthesis pathways, and such mutations may occur artificially, for example, by UV irradiation, but not exclude natural mutations.

Specifically, the target substance-producing microorganism may be modified to produce the target substance. For example, a microorganism having no ability to produce a target substance may be modified to have a producing ability of the target substance, or the producing ability of the microorganism may be enhanced. As an example, proteins or variants thereof involved in biosynthesis pathways may be introduced into wild-type microorganisms for production of target substances (KR 10-2011994, KR 10-1947959, and KR 10-1996769).

As a specific example, the target substance-producing microorganism of the present disclosure may be a microorganism of the genus *Corynebacterium* containing aspartokinase (lysC), homoserine dehydrogenase (hom), pyruvate carboxylase (pyc), L-threonine dehydratase (ilvA), or a combination thereof. The aspartokinase, homoserine dehydrogenase, pyruvate carboxylase, or L-threonine dehydratase may be a wild-type protein or may be a protein variant that is mutated to benefit the production of a target substance through the attenuation or enhancement of activity.

The microorganism of the present disclosure may have a target substance producing ability enhanced by at least 1%, 5%, 10%, 13%, 14%, 15%, 16%, 17%, 18%, 19%, 20%, 22%, 25%, 29%, 33%, 38%, 44%, 45%, or 48% compared with microorganisms not including the polynucleotide having promoter activity.

In accordance with still another aspect of the present disclosure, there is provided a method for producing a target substance, the method including culturing the microorganism in a medium. The microorganism and target substance are as described above.

In the present disclosure, the method for producing a target substance by using the microorganisms including the polynucleotide may be performed using a method widely known in the art. Specifically, the culture may be performed continuously through a batch process or a fed batch or repeated fed batch process, but is not limited thereto. The media used in the culture must appropriately satisfy the requirements of specific strains. The culture media for strains of the genus *Corynebacterium* are disclosed (e.g., *Manual of Methods for General Bacteriology by the American Society for Bacteriology*, Washington D.C., USA, 1981).

As for the media and other culture conditions used for culturing the strains of the present disclosure, any medium that is used for the culture of typical microorganisms of the genus *Corynebacterium* may be used without particular limitation. Specifically, the strains of the present disclosure may be cultured under aerobic or anaerobic conditions in conventional media containing appropriate carbon sources, nitrogen sources, phosphorus sources, inorganic compounds, amino acids, and/or vitamins, while the temperature, pH, and the like are adjusted.

In the present disclosure, the carbon sources may include: carbohydrates, such as glucose, fructose, sucrose, and maltose; sugar alcohols, such as mannitol and sorbitol; organic acids, such as pyruvic acid, lactic acid, and citric acid; amino acids, such as glutamate, methionine, and lysine; and the like, but are not limited thereto. In addition, natural organic nutrient sources, such as starch hydrolysates, molasses, blackstrap molasses, rice bran, cassava, bagasse, and corn steep liquor, may be used, and carbohydrates, such as glucose and sterile pretreated molasses (i.e., molasses converted to reduced sugars) may be used, and appropriate amounts of other carbon sources may be used without limitation. These carbon sources may be used alone or in a combination of two or more thereof.

Examples of the nitrogen sources may include: inorganic nitrogen sources, such as ammonia, ammonium sulfate, ammonium chloride, ammonium acetate, ammonium phosphate, ammonium carbonate, and ammonium nitrate; and organic nitrogen sources, such as amino acids, peptone, NZ-amine, meat extracts, yeast extracts, malt extracts, corn steep liquor, casein hydrolysates, fishes or their degraded products, defatted soybean cake or its degraded products. These nitrogen sources may be used alone or in combination of two or more, but are not limited thereto.

Examples of the phosphorus sources may include potassium phosphate monobasic, potassium phosphate dibasic, and sodium-containing salts corresponding thereto. Examples of the inorganic compounds may include sodium chloride, calcium chloride, iron chloride, magnesium sulfate, iron sulfate, manganese sulfate, calcium carbonate, and the like.

Furthermore, the medium may contain amino acids, vitamins, and/or appropriate precursors. Specifically, an L-amino acid or the like may be added to the culture medium of the strain. Specifically, glycine, glutamate, and/or cysteine may be added, and if necessary, an L-amino acid, such as lysine, may be further added, but not necessarily limited thereto.

These media or precursors may be added to cultures in a batch or continuous manner, but are not limited thereto.

In the present disclosure, during the culture of strains, the pH of the cultures may be adjusted by adding compounds, such as ammonium hydroxide, potassium hydroxide, ammonia, phosphoric acid, and sulfuric acid, to the cultures in an appropriate manner. In addition, an antifoaming agent, such as fatty acid polyglycol ester, may be added to suppress foam formation during the culture. In order to maintain aerobic states of the cultures, oxygen or oxygen-containing gas may be injected into the cultures, or in order to maintain anaerobic or non-aerobic states, no gas is injected, or nitrogen, hydrogen, or carbon dioxide gas may be injected.

The temperature of the cultures may be 25° C. to 40° C., and specifically 28° C. to 37° C., but is not limited thereto. The duration of culture may be continued until the desired production amount of a useful substance can be obtained, and may be specifically 1 to 160 hours, or 10 to 100 hours, but is not limited thereto.

The method for producing a target substance may further include an additional process after the culturing step. The additional process may be appropriately selected according to use of the target substance.

Specifically, the method for producing a target substance may include, after the culturing step, recovering the target substance from at least one selected from the microorganism, the medium, a dried product of the microorganism, an extract of the microorganism, a culture of the microorganism, a supernatant of the culture, and a lysate of the microorganism.

The method may further include, before or simultaneously with the recovery step, lysing the microorganism (strain). The lysis of the strain may be performed by a method commonly used in the art to which the present disclosure belongs, for example, a lysis buffer, a sonicator, heat treatment, a French press, and the like. In addition, the lysis step may include an enzymatic reaction by a cell wall degrading enzyme, a nucleic acid degrading enzyme, a nucleic acid transfer enzyme, a proteolytic enzyme, or the like, but is not limited thereto.

In the present disclosure, the term "dried product of microorganism" may be used interchangeably with the term "strain dried product" or the like. The dried product of the microorganism may be prepared by drying cells accumulating a target substance therein, and specifically may be included in a feed composition, a food composition, and the like, but is not limited thereto.

In the present disclosure, the extract of microorganism may be used interchangeably with the term "strain extract" or the like. The strain extract may refer to a material remaining after the separation of cell walls from the cells of the strain. Specifically, the strain extract may refer to the other components excluding the cell walls from the components obtained by lysis of the cells. The strain extract contains a target substance, and may contain at least one component of proteins, carbohydrates, nucleic acids, and fibers, in addition to the target substance, but is not limited thereto.

In the recovery step, a target substance may be recovered using an appropriate method known in the art.

The recovery step may include a purification process. The purification process may be that only a target substance is separated from the strain, followed by pure purification. Through the purification process, the purely purified target substance can be produced.

As needed, the method for producing a target substance may further include mixing an excipient and a material selected from a strain obtained after the culturing step, or a dried product, extract, culture, or lysate thereof, and a target substance recovered therefrom.

The excipient may be used by appropriate selection according to the intended use or form, and may be selected from starch, glucose, cellulose, lactose, glycogen, D-mannitol, sorbitol, lactitol, maltodextrin, calcium carbonate, synthetic aluminum silicate, calcium monohydrogen phosphate, calcium sulfate, sodium chloride, sodium hydrogen carbonate, purified lanolin, dextrin, sodium alginate, methyl cellulose, colloidal silica gel, hydroxypropyl starch, hydroxypropyl methyl cellulose, propylene glycol, casein, calcium lactate, Primojel, and gum arabic. Specifically, the excipient may be at least one component selected from starch, glucose, cellulose, lactose, dextrin, glycogen, D-mannitol, and maltodextrin, but is not limited thereto.

Examples of the excipient may include a preservative, a wetting agent, a dispersing agent, a suspending agent, a buffering agent, a stabilizing agent, an isotonic agent, or the like, but are not limited thereto.

In accordance with another aspect of the present disclosure, there is provided use of a polynucleotide as a promoter, the polynucleotide having promoter activity, in which the nucleotides at positions 27, 28, 31, 32, and 36 are substituted with other nucleotides in the polynucleotide sequence of SEQ ID NO: 1.

The polynucleotide is as described above.

Mode for Carrying Out the Invention

Hereinafter, the present disclosure will be described in more detail with reference to exemplary embodiments. However, these exemplary embodiments are given for specifically illustrating the present disclosure, and the scope of the present disclosure is not limited to these examples.

Example 1: Identification of Activity of Novel Promoter to Induce Target Gene Expression

Example 1-1. Mutant Library of gdh Promoter Using Random Mutagenesis

First, the nucleotide sequence (SEQ ID NO: 1) containing a promoter region of gdh gene (NCBI accession number NCgl1999) of the wild-type *Corynebacterium glutamicum* ATCC13032 was secured on the basis of the NIH GenBank. The gdh promoter mutant PCR products (Pmgdh) with different sequences were obtained by using the promoter of the gdh gene consisting of the nucleotide sequence of SEQ ID NO: 1 as a template along with the primers of SEQ ID NO: 5 and SEQ ID NO: 6, and the Diversify PCR Random Mutagenesis Kit (TakaRa) was used. As for the open reading frame (ORF) of GFP gene, PCR was performed by using the pGFPuv vector (Clontech, USA) as a template along with the primers of SEQ ID NOS: 7 and 8. PCR was performed with denaturation at 94° C. for 5 minutes, 30 cycles of denaturation at 94° C. for 30 seconds, annealing at 55° C. for 30 seconds, and polymerization at 72° C. for 1 minute, and then a polymerization reaction at 72° C. for 7 minutes, thereby obtaining gene fragments containing ORF of GFP.

The gdh promoter mutant PCR products (Pmgdh) and GFP, which were amplification products, were mixed with pCES208, which was an *E. coli-Corynebacterium* shuttle vector prepared by cleavage with BamHI/SalI restriction enzymes (*J. Microbiol. Biotechnol.* 18:639-647, 2008), to construct a recombinant vector library in which Pmgdh was linked with GFP, by using the In-Fusion® HD cloning kit (Clontech). The respective vectors were named from pCES_Pm1gdh_gfp to pCES_Pm100gdh_gfp.

As a control for investigating the activity of Pmgdh library, a recombinant vector in which the promoter (SEQ ID NO: 1) of the wild-type gdh gene was linked with GFP was used. The promoter gene fragments of the wild-type gdh gene were obtained by using the wild-type *Corynebacterium glutamicum* ATCC13032 as a template along with the primers of SEQ ID NO: 5 and SEQ ID NO: 6. As for the open reading frame (ORF) of GFP gene, PCR was performed by using the pGFPuv vector (Clontech, USA) as a template along with the primers of SEQ ID NOS: 7 and 8. PCR was performed with denaturation at 94° C. for 5 minutes, 30 cycles of denaturation at 94° C. for 30 seconds, annealing at 55° C. for 30 seconds, and polymerization at 72° C. for 1 minute, and then a polymerization reaction at 72° C. for 7 minutes, thereby obtaining gene fragments containing ORF of GFP.

The gdh wild-type promoter PCR products (Pgdh) and GFP, which were amplification products, were mixed with pCES208, which was an *E. coli-Corynebacterium* shuttle vector prepared by cleavage with BamHI/SalI restriction enzymes (*J. Microbiol. Biotechnol.* 18:639-647, 2008), to construct a recombinant vector in which Pgdh was linked with GFP, by using the In-Fusion® HD cloning kit (Clontech), and this recombinant vector was named pCES_Pgdh_gfp.

Example 1-2. Preparation of Transformed Strains

The vector pCES208, and the recombinant vector pCES_Pmgdh_gfp library (pCES_Pm1gdh_gfp to pCES_Pm100gdh_gfp) and pCES_Pgdh_gfp, which were constructed in Example 1-1, were transformed into the *Corynebacterium glutamicum* ATCC13032 by electroporation (*Appl. Microbiol. Biotechnol.* (1999) 52:541-545). Then, the transformed strains were selected in selective media containing 25 mg/L and kanamycin, named ATCC13032/pCES, ATCC13032/pCES_Pmgdh_gfp (ATCC13032/pCES_Pm1gdh_gfp to ATCC13032/pCES_Pm100gdh_gfp), and ATCC13032/pCES_Pgdh_gfp, respectively.

Example 1-3. Selection of gdh Promoter Mutants

To investigate the activity of gdh promoter mutants, the *Corynebacterium glutamicum* ATCC13032/pCES, ATCC13032/pCES_Pgdh_gfp, and ATCC13032/pCES_Pmgdh_gfp (ATCC13032/pCES_Pm1gdh_gfp to ATCC13032/pCES_Pm100gdh_gfp), which were the transformed strains obtained in Example 1-2, were cultured by way of the following method and measured for GFP activity.

Specifically, the transformed *Corynebacterium glutamicum* strains each were inoculated into a flask containing 25 mL of a medium (20 g of glucose, 5 g of ammonium sulfate, 5 g of yeast extract, 1.5 g of urea, 4 g of $KH_2PO_4$, 8 g of $K_2HPO_4$, 0.5 g of $MgSO_4 \cdot 7H_2O$, 150 μg of biotin, 1.5 mg of thiamine hydrochloride, 3 mg of calcium pantothenate, 3 mg of nicotinamide (based on 1 L of distilled water), pH 7.2) and cultured with shaking at 30° C. for 20 hours. The cells were recovered from the cultures by centrifugation (5,000 rpm, 15 minutes), washed twice with 50 mM Tris-HCl (pH 8.0) buffer, and then suspended in the same buffer. After 1.25 g of glass beads were added per 1.5 mL of the suspension, the cells were disrupted using a bead beater for 6 minutes. Then, the supernatant was recovered by centrifugation (15,000 rpm, 20 minutes), and the concentrations of proteins were quantitated by the Bradford method. For an equal amount of cell extracts, the excited light was irradiated at 488 nm by using a method introduced by Laure Gory et al. (*FEMS Microbiology Letters,* 194, 127-133, 2001), and the emitted light at 511 nm was measured using the LS-50B spectrophotometer (Perkin-Elmer), and thus the expression level of the GFP gene was measured. Through the comparison with the GFP gene expression level of the control ATCC13032/pCES_Pgdh_gfp strain, the top three strains with the highest GFP gene expression levels were selected (Table 1).

TABLE 1

| Strain | Fluorescence sensitivity |
|---|---|
| ATCC13032/pCES | 0 |
| ATCC13032/pCES_Pgdh_gfp | 583 |
| ATCC13032/pCES_Pm3gdh_gfp | 1217 |
| ATCC13032/pCES_Pm16gdh_gfp | 1205 |
| ATCC13032/pCES_Pm78gdh_gfp | 1198 |

As shown in Table 1 above, the Pm3gdh, Pm16gdh, and Pm78gdh promoters showed promoter activity in *Corynebacterium glutamicum*, and also showed higher fluorescence sensitivity than the wild type gdh promoter. In order to investigate the mutation introduced into the gdh promoters of the three types of strains selected above, the gdh promoter mutants were sequenced. After PCR was performed using the primers of SEQ ID NO: 9 and SEQ ID NO: 10 to determine sequences, sequencing was performed. A comparison with the sequence of SEQ ID NO: 1, which is the wild-type gdh promoter sequence, was made, and thus the modified gdh promoters were sequenced. The sequences of the gdh promoters of the selected strains are shown in Table 2 below (Table 2).

TABLE 2

| SEQ ID NO | Mutant | Sequence |
|---|---|---|
| 2 | Pm3gdh | ATTCTTTGTGGTCATATCTGTGCGACTGTGGTATACTTGAACGT GAGCATTTACCAGCCTAAATGCCCGCAGTGAGTTAAGTCTCAAA GCAAGAAGTTGCTCTTTAGGGCATCCGTAGTTTAAAACTATTAA CCGTTAGGTATGACAAGCCGGTTGATGTGAACGCAGTTTTTAAA AGTTTCAGGATCAGATTTTTCACAGGCATTTTGCTCCAGCAAAC GCCTAGGATGTACATGGTGCCCTCAATGGGAACCACCAACATCA CTAAATGGCCCAGGTACACACTTTAAAATCGTGCGCGCATGCAG CCGAGATGGGAACGAGGAAATC |
| 3 | Pm16gdh | ATTCTTTGTGGTCATATCTGTGCGACTGTGGTATACTTGAACGT GAGCATTTACCAGCCTAAATGTCCGCAGTGAGTTAAGTCTCAAA GCAAGAAGTTGCTCTTTAGGGCATCCGTAGTTTAAAACTATTAA CCGTTAGGTATGACAAGCCGGTTGATGTGAACGCAGTTTTTAAA AGTTTCAGGATCAGATTTTTCACAGGCATTTTGCTCCAGCAAAC GCCTAGGATGTACATGGTGCCCTCAATGGGAACCACCAACGTCA CTAAATGGCCCAGGTACACACTTTAAAATCGTGCGCGCATGCAG CCGAGATGGGAACGAGGAAATC |
| 4 | Pm78gdh | ATTCTTTGTGGTCATATCTGTGCGACTGTGGTATACTTGAACGT GAGCATTTACCAGCCTAAATGTCCGCAGTGAGTTAAGTCTCAAA GCAAGAAGTTGCTCTTTAGGGCATCCGTAGTTTAAAACTATTAA CCGTTAGGTATGACAAGCCGGTTGATGTGAACGCAGTTTTTAAA AGTTTCAGGATCAGATTTTTCACAGGCATTTTGCTCCAGCAAAC GCCTAGGATGTACATGGTGCCCTCAATGGGAACCACCAACATCA CTAAATGGCCCAGGTACACACTTTAAAATCGTGCGCGCATGCAG CCGAGATGGGAACGAGGAAATC |

Example 2: Construction of Xectors for Introduction of Pm3gdh, Pm16gdh, and Pm78gdh Promoter Mutants In order to construct vectors for introduction of Pm3gdh, Pm16gdh, and Pm78gdh promoter mutants, PCR products corresponding to the promoter mutants were obtained by the pCES_Pm3gdh_gfp, pCES_Pm16gdh_gfp, and pCES_Pm78gdh_gfp vectors as templates, respectively, along with the primers of SEQ ID NO: 13 and SEQ ID NO: 14. The gene fragments containing the gdh promoter upstream region and a part of ORF of gdh were obtained by using the chromosome of the *Corynebacterium glutamicum* ATCC13032 strain as a template along with the primer set of SEQ ID NO: 11 and SEQ ID NO: 12 and SEQ ID NO: 15 and SEQ ID NO: 16. PCR was performed with denaturation at 94° C. for 5 minutes, 30 cycles of denaturation at 94° C. for 30 seconds, annealing at 55° C. for 30 seconds, and polymerization at 72° C. for 1 minute, and then a polymerization reaction at 72° C. for 5 minutes, thereby obtaining respective PCR products. The three amplification products were mixed with pDCM2 vector, which was prepared in advance by cleavage with SmaI restriction enzyme (Korean Patent Publication No. 10-2020-0136813), to construct recombinant vectors by using the In-Fusion® HD cloning kit (Clontech), and these vectors were named pDCM2_Pm3gdh_gdh, pDCM2_Pm16gdh_gdh, and pDCM2_Pm78gdh_gdh, respectively.

Example 3: Evaluation of Target Substance Producing Ability

3-1. Evaluation of Lysine Producing Ability

3-1-1. Preparation of L-lysine Producing Strains Introduced with gdh Promoter Mutants To prepare strains into which gdh promoter mutants were transformed, by using the pDCM2_Pm3gdh_gdh, pDCM2_Pm16gdh_gdh, and pDCM2_Pm78gdh_gdh vectors constructed in Example 2, the vectors were transformed into the L-lysine-producing strain *Corynebacterium glutamicum* CJ3P (Binder et al. Genome Biology 2012, 13:R40) to introduce gdh promoter mutant sequences into the chromosome. The CJ3P strain is a *Corynebacterium glutamicum* strain having L-lysine producing ability by introduction of three types of mutations (pyc(Pro458Ser), hom(Val59Ala), and lysC(Thr311Ile)) into the wild-type strain on the basis of known techniques.

Specifically, the vectors constructed in Example 2 were introduced into CJ3P strain by electroporation, and then transformed strains were obtained from selective media containing 25 mg/L kanamycin. The strains, into which gdh promoter mutants were introduced by DNA fragments inserted into the chromosome through secondary cross-over, were selected by PCR using the primers of SEQ ID NO: 9 and SEQ ID NO: 10 and sequencing, and the selected strains were named *Corynebacterium glutamicum* CJ3P::Pm3gdh_gdh, CJ3P::Pm16gdh_gdh, and CJ3P::Pm78gdh_gdh.

3-1-2. Evaluation of L-lysine Producing Ability of Strains Introduced with gdh Promoter Mutants To evaluate the L-lysine producing ability of the *Corynebacterium glutamicum* CJ3P strain used as a parent strain and the *Corynebacterium glutamicum* CJ3P::Pm3gdh_gdh, CJ3P::Pm16gdh_gdh, and CJ3P::Pm78gdh_gdh strains prepared in Example 3-1-1, the strains were cultured by way of the following method and then analyzed.

First, the strains each were inoculated into a 250 mL corner-baffle flask containing 25 mL of a seed medium and cultured with shaking at 200 rpm for 20 hours at 30° C. Then, 1 mL of the seed culture was inoculated into a 250 mL corner-baffle flask containing 24 mL of a production medium and cultured with shaking at 200 rpm for 48 hours at 32° C. The compositions of the seed medium and production medium were as below.

<Seed Medium (pH 7.0)>

20 g of glucose, 10 g of peptone, 5 g of yeast extract, 1.5 g of urea, 4 g of $KH_2PO_4$, 8 g of $K_2HPO_4$, 0.5 g of $MgSO_4 \cdot 7H_2O$, 100 μg of biotin, 1000 μg of thiamine hydrochloride, 2000 μg of calcium pantothenate, and 2000 μg of nicotinamide (based on 1 L of distilled water)

<Production Medium (pH 7.0)>

45 g of glucose, 10 g of soy bean protein, 10 g of molasses, 15 g of $(NH_4)_2SO_4$, 0.55 g of $KH_2PO_4$, 0.6 g of $MgSO_4 \cdot 7H2O$, 9 mg of $FeSO_4 \cdot 7H_2O$, 9 mg of $MnSO_4 \cdot 5H_2O$, 0.9 mg of biotin, 4.5 mg of thiamine hydrochloride, 30 g of $CaCO_3$, 4.5 mg of calcium pantothenate, 30 mg of nicotinamide, 0.45 mg of $ZnSO_4$, and 0.45 mg of $CuSO_4$ (based on 1 L of distilled water)

After the completion of the culture, the amount of L-lysine produced was measured using HPLC. The L-lysine concentration and concentration increase rate in the culture for each of the *Corynebacterium glutamicum* CJ3P, CJ3P::Pm3gdh_gdh, CJ3P::Pm16gdh_gdh, and CJ3P::Pm78gdh_gdh strains are shown in Table 3 below.

TABLE 3

| Strain name | L-Lysine concentration (g/L) | L-Lysine concentration increase rate (%) |
|---|---|---|
| CJ3P | 4.12 | — |
| CJ3P::gdhPm3_gdh | 4.96 | 20.39% |
| CJ3P::gdhPm16_gdh | 4.84 | 17.48% |
| CJ3P::gdhPm78_gdh | 4.79 | 16.26% |

As shown in Table 3, three strains introduced with gdh promoter mutants showed an increase in L-lysine concentration compared with the parent strain CJ3P. CJ3P::gdhPm3_gdh was named CM03-1660, which was deposited with the Korea Microorganism Conservation Center, a depository institution under the Budapest Treaty, on Apr. 5, 2021 and given the accession number KCCM12970P.

Example 3-2: Evaluation of Threonine Producing Ability

3-2-1. Preparation of Threonine-Producing Strains

To prepare strains transformed with gdh promoter mutants by using the pDCM2_Pm3gdh_gdh, pDCM2_Pm16gdh_gdh, and pDCM2_Pm78gdh_gdh vectors constructed in Example 2, L-threonine-producing strains introduced with a lysC(L377K) mutant (Korean Patent No. 10-2011994) and a hom(R398Q) mutant (Korean Patent No. 10-1947959) were first prepared on the basis of the *Corynebacterium glutamicum* ATCC13032 strain.

Specifically, to prepare L-threonine-producing strains, a vector for introduction of lysC(L377K) was first constructed. To construct the vector, PCR was performed by the chromosome of the wild-type *Corynebacterium glutamicum* ATCC13032 strain as a template along with the primers of SEQ ID NOS: 17 and 18 and SEQ ID NOS: 19 and 20. PCR was performed with denaturation at 95° C. for 5 minutes, 30 cycles of denaturation at 95° C. for 30 seconds, annealing at 55° C. for 30 seconds, and polymerization at 72° C. for 30 seconds, and then a polymerization reaction at 72° C. or 7 minutes, thereby obtaining respective PCR products. The amplification products were mixed with pDCM2 vector, which was prepared in advance by cleavage with SmaI restriction enzyme, to construct a recombinant vector by using the In-Fusion® HD cloning kit, and then the vector was named pDCM2_lysC(L377K).

The constructed pDCM2_lysC(L377K) vector was introduced into the *Corynebacterium glutamicum* ATCC13032 strain by electroporation, and then the transformed strain was obtained in a selective medium containing 25 mg/L kanamycin. The strains, into which a nucleotide mutant was introduced in the lysC gene by DNA fragments inserted into the chromosome through secondary cross-over, were selected by PCR using the primers of SEQ ID NO: 25 and SEQ ID NO: 26 and sequencing, and the selected strain was named ATCC13032:lysC(L377K).

To construct the vector for introduction of hom(R398Q), PCR was performed by the chromosome of the *Corynebacterium glutamicum* ATCC13032 strain as a template along with the primers of SEQ ID NOS: 21 and 22 and SEQ ID NOS: 23 and 24. PCR was performed under PCR conditions of denaturation at 95° C. for 5 minutes, 30 cycles of denaturation at 95° C. for 30 seconds, annealing at 55° C. for 30 seconds, and polymerization at 72° C. for 30 seconds, and then a polymerization reaction at 72° C. for 7 minutes. The amplification products were mixed with pDCM2 vector, which was prepared in advance by cleavage with SmaI restriction enzyme, to construct a recombinant vector by using the In-Fusion® HD cloning kit, and then the vector was named pDCM2_hom(R398Q).

The constructed pDCM2_hom(R398Q) vector was introduced into the *Corynebacterium glutamicum* ATCC13032::lysC(L377K), strain prepared above, by electroporation, and then the transformed strain was obtained in a selective medium containing 25 mg/L kanamycin. The strains, into which a nucleotide mutant was introduced in the hom gene by DNA fragments inserted into the chromosome through secondary cross-over, were selected by PCR using the primers of SEQ ID NO: 27 and SEQ ID NO: 28 and sequencing, and the selected strain was named *Corynebacterium glutamicum* ATCC13032::lysC(L377K)_hom(R398Q).

3-2-2. Preparation of L-threonine-Producing Strains Introduced with gdh Promoter Mutants Specifically, the vectors constructed in Example 2 were introduced into the *Corynebacterium glutamicum* ATCC13032::lysC(L377K)_hom(R398Q) strain by electroporation, and then transformed strains were obtained from selective media containing 25 mg/L kanamycin. The strains, into which gdh promoter mutants were introduced by DNA fragments inserted into the chromosome through secondary cross-over, were selected by PCR using the primers of SEQ ID NO: 9 and SEQ ID NO: 10 and sequencing, and the selected strains were named *Corynebacterium glutamicum* ATCC13032::lysC(L377K)_hom(R398Q)::Pm3gdh_gdh, ATCC13032::lysC(L377K)_hom(R398Q)::Pm16gdh_gdh, and ATCC13032::lysC(L377K)_hom(R398Q)::Pm78gdh_gdh.

3-2-3. Evaluation of L-threonine Producing Ability of Strains Introduced with gdh Promoter Mutants To evaluate the L-threonine producing ability of the *Corynebacterium glutamicum* ATCC13032::lysC(L377K)_hom(R398Q) used as a parent strain and the *Corynebacterium glutamicum* ATCC13032::lysC(L377K)_hom(R398Q)::Pm3gdh_gdh, ATCC13032::lysC(L377K)_hom(R398Q)::Pm16gdh_gdh, and ATCC13032::lysC(L377K)_hom(R398Q)::Pm78gdh_gdh strains prepared in Example 3-2-2, the strains were cultured by way of the following method and then analyzed.

First, the strains each were inoculated into a 250 mL corner-baffle flask containing 25 mL of a seed medium and cultured with shaking at 200 rpm for 20 hours at 30° C. Then, 1 mL of the seed culture was inoculated into a 250 mL corner-baffle flask containing 24 mL of a production medium and cultured with shaking at 200 rpm for 48 hours at 32° C. The compositions of the seed medium and production medium were as below.

<Seed Medium (pH 7.0)>

20 g of glucose, 10 g of peptone, 5 g of yeast extract, 1.5 g of urea, 4 g of $KH_2PO_4$, 8 g of $K_2HPO_4$, 0.5 g of $MgSO_4 \cdot 7H_2O$, 100 μg of biotin, 1000 μg of thiamine hydrochloride, 2000 μg of calcium pantothenate, and 2000 μg of nicotinamide (based on 1 L of distilled water)

<Production Medium (pH 7.0)>

45 g of glucose, 10 g of soy bean protein, 10 g of molasses, 15 g of $(NH_4)_2SO_4$, 0.55 g of $KH_2PO_4$, 0.6 g of $MgSO_4 \cdot 7H_2O$, 9 mg of $FeSO_4 \cdot 7H_2O$, 9 mg of $MnSO_4 \cdot 5H_2O$, 0.9 mg of biotin, 4.5 mg of thiamine hydrochloride, 30 g of $CaCO_3$, 4.5 mg of calcium pantothenate, 30 mg of nicotinamide, 0.45 mg of $ZnSO_4$, and 0.45 mg of $CuSO_4$ (based on 1 L of distilled water)

After the completion of the culture, the amount of L-threonine produced was measured using HPLC. The L-threonine concentration and concentration increase rate in the culture for each of the *Corynebacterium glutamicum* ATCC13032::lysC(L377K)_hom(R398Q), ATCC13032::lysC(L377K)_hom(R398Q)::Pm3gdh_gdh, ATCC13032::lysC(L377K)_hom(R398Q)::Pm16gdh_gdh, and ATCC13032::lysC(L377K)_hom(R398Q)::Pm78gdh_gdh strains are shown in Table 4 below.

TABLE 4

| Strain name | L-Threonine concentration (g/L) | L-Threonine concentration increase rate (%) |
|---|---|---|
| ATCC13032::lysC(L377K)_hom(R398Q) | 0.83 | — |
| ATCC13032::lysC(L377K)_hom(R398Q)::Pm3gdh_gdh | 1.11 | 33.73% |
| ATCC13032::lysC(L377K)_hom(R398Q)::Pm16gdh_gdh | 0.95 | 14.46% |
| ATCC13032::lysC(L377K)_hom(R398Q)::Pm78gdh_gdh | 1.02 | 22.89% |

As shown in Table 4, three strains introduced with gdh promoter mutants showed an increase in L-threonine concentration compared with the parent strain ATCC13032::lysC(L377K)_hom(R398Q).

Example 3-3: Evaluation of O-acetyl Homoserine Producing Ability 3-3-1. Preparation of O-acetyl Homoserine-Producing Strains Introduced with gdh Promoter Mutants The vectors constructed in Example 2 were introduced into the wild-type strain *Corynebacterium glutamicum* ATCC13032 by electroporation, and then transformed strains were obtained from selective media containing 25 mg/L kanamycin. The strains, into which gdh promoter mutants were introduced by DNA fragments inserted into the chromosome through secondary cross-over, were selected by PCR using the primers of SEQ ID NO: 9 and SEQ ID NO: 10 and sequencing, and the selected strains were named *Corynebacterium glutamicum* ATCC13032::Pm3gdh_gdh, ATCC13032::Pm 16gdh_gdh, and ATCC13032::Pm78gdh_gdh.

3-3-2. Evaluation of O-acetyl Homoserine Producing Ability of Strains Introduced with gdh Promoter Mutants To evaluate the O-acetyl homoserine producing ability of the *Corynebacterium glutamicum* ATCC13032 used as a parent strain and the ATCC13032::Pm3gdh_gdh, ATCC13032::Pm16gdh_gdh, and ATCC13032::Pm78gdh_gdh strains prepared in Example 3-3-1, the strains were cultured by way of the following method and then analyzed.

The strains each were inoculated into a 250 mL corner-baffled flask containing 25 mL of the following medium using an inoculation loop, and then cultured with shaking at 200 rpm for 20 hours at 33° C.

<Production Medium (pH 7.2)>

30 g of glucose, 2 g of $KH_2PO_4$, 3 g of urea, 40 g of $(NH_4)_2SO_4$, 2.5 g of peptone, 5 g (10 mL) of corn steep liquor (CSL, Sigma), 0.5 g of $MgSO_4 \cdot 7H_2O$, and 20 g of $CaCO_3$ (based on 1 L of distilled water)

After the completion of the culture, the O-acetyl homoserine producing ability was measured by HPLC. The O-acetyl homoserine concentration and concentration increase rate in the culture for each of the *Corynebacterium glutamicum* ATCC13032, ATCC13032::Pm3gdh_gdh, ATCC13032::Pm16gdh_gdh, and ATCC13032::Pm78gdh_gdh strains are shown in Table 5 below.

TABLE 5

| Strain name | O-Acetyl homoserine concentration (g/L) | O-Acetyl homoserine concentration increase rate (%) |
|---|---|---|
| ATCC13032 | 0.31 | — |
| ATCC13032::Pm3gdh_gdh | 0.45 | 45.16% |
| ATCC13032::Pm16gdh_gdh | 0.39 | 25.80% |
| ATCC13032::Pm78gdh_gdh | 0.43 | 38.70% |

As shown in Table 5, three strains introduced with gdh promoter mutants showed an increase in O-acetyl homoserine concentration compared with the parent strain wild-type strain ATCC13032.

Example 3-4: Evaluation of L-isoleucine Producing Ability 3-4-1. Preparation of L-isoleucine-Producing Strains Introduced with gdh Promoter Mutants To prepare strains into which gdh promoter mutants were transformed, by using the pDCM2_Pm3gdh_gdh, pDCM2_Pm16gdh_gdh, and pDCM2_Pm78gdh_gdh vectors constructed in Example 2, the vectors were first transformed into the *Corynebacterium glutamicum* CJP1 (Korean Patent No. 10-1996769), to introduce gdh promoter mutant sequences into the chromosome. Thereafter, a vector including ilvA gene (V323A) in which valine is substituted with alanine at the 323rd amino acid in the known ilvA gene encoding L-threonine dehydratase (*Appl. Enviro. Microbiol.*, Dec. 1996, p. 4345-4351) was further introduced to prepare an L-isoleucine-producing strain (Korean Patent No. 10-1996769).

Specifically, the vectors constructed in Example 2 were introduced into CJP1 strain by electroporation, and then transformed strains were obtained from selective media containing 25 mg/L kanamycin. The strains, into which gdh promoter mutants were introduced by DNA fragments inserted into the chromosome through secondary cross-over, were selected by PCR using the primers of SEQ ID NO: 9 and SEQ ID NO: 10 and sequencing, and the selected strains were named *Corynebacterium glutamicum* CJP1::Pm3gdh_gdh, CJP1::Pm16gdh_gdh, and CJP1::Pm78gdh_gdh.

The pECCG117-ilvA(V323A) vector (Korean Patent No. 10-1996769) was introduced into the prepared strains by electroporation, and then transformed strains were obtained from selective media containing 25 mg/L kanamycin. The selected strains are named CJP1::Pm3gdh_gdh/pECCG117-ilvA(V323A), CJP1::Pm16gdh_gdh/pECCG117-ilvA (V323A), and CJP1::Pm78gdh_gdh/pECCG117-ilvA (V323A), respectively.

3-4-2. Evaluation of L-isoleucine Producing Ability of Strains Introduced with gdh Promoter Mutants To evaluate the L-isoleucine producing ability of the *Corynebacterium glutamicum* CJP1/pECCG117-ilvA (V323A) used as a parent strain and the CJP1::Pm3gdh_gdh/pECCG117-ilvA(V323A), CJP1::Pm16gdh_gdh/pECCG117-ilvA(V323A), and CJP1::Pm78gdh_gdh/pECCG117-ilvA(V323A) strains prepared in Example 3-4-1, the strains were cultured by way of the following method and then analyzed.

First, the strains each were inoculated into a 250 mL corner-baffle flask containing 25 mL of a seed medium and cultured with shaking at 200 rpm for 20 hours at 30° C. Then, 1 mL of the seed culture was inoculated into a 250 mL corner-baffle flask containing 24 mL of a production medium and cultured with shaking at 200 rpm for 48 hours at 32° C. The compositions of the seed medium and production medium were as below.

<Seed Medium (pH 7.0)>

20 g of glucose, 10 g of peptone, 5 g of yeast extract, 1.5 g of urea, 4 g of $KH_2PO_4$, 8 g of $K_2HPO_4$, 0.5 g of $MgSO_4 \cdot 7H_2O$, 100 µg of biotin, 1000 µg of thiamine hydrochloride, 2000 µg of calcium pantothenate, and 2000 µg of nicotinamide (based on 1 L of distilled water)

<Production Medium (pH 7.0)>

45 g of glucose, 10 g of soy bean protein, 10 g of molasses, 15 g of $(NH_4)_2SO_4$, 0.55 g of $KH_2PO_4$, 0.6 g of $MgSO_4 \cdot 7H_2O$, 9 mg of $FeSO_4 \cdot 7H_2O$, 9 mg of $MnSO_4 \cdot 5H_2O$, 0.9 mg of biotin, 4.5 mg of thiamine hydrochloride, 30 g of $CaCO_3$, 4.5 mg of calcium pantothenate, 30 mg of nicotinamide, 0.45 mg of $ZnSO_4$, and 0.45 mg of $CuSO_4$ (based on 1 L of distilled water)

After the completion of the culture, the amount of L-isoleucine produced was measured using HPLC. The L-isoleucine concentration and concentration increase rate in the culture for each of the *Corynebacterium glutamicum* CJP1/pECCG117-ilvA(V323A), CJP1::Pm3gdh_gdh/pECCG117-ilvA(V323A), CJP1::Pm16gdh_gdh/pECCG117-ilvA(V323A), and CJP1::Pm78gdh_gdh/pECCG117-ilvA(V323A) strains are shown in Table 6 below.

TABLE 6

| Strain name | L-Isoleucine concentration (g/L) | L-Isoleucine concentration increase rate (%) |
|---|---|---|
| CJP1/pECCG117-ilvA(V323A) | 0.74 | — |
| CJP1::Pm3gdh_gdh/pECCG117-ilvA(V323A) | 1.10 | 48.65% |
| CJP1::Pm16gdh_gdh/pECCG117-ilvA(V323A) | 0.96 | 29.73% |
| CJP1::Pm78gdh_gdh/pECCG117-ilvA(V323A) | 1.07 | 44.59% |

As shown in Table 6, three strains introduced with gdh promoter mutants showed an increase in L-isoleucine concentration compared with the parent strain wild-type strain CJP1/pECCG117-ilvA(V323A).

The above results identified that the recombinant microorganisms including the polynucleotide having promoter activity of the present disclosure increased the productivity of L-lysine, L-threonine, O-acetyl homoserine, and L-isoleucine useful for industry.

From the above description, a person skilled in the art to which the present disclosure pertains will be able to understand that the present disclosure may be embodied in other specific forms without departing from the technical spirit or essential characteristics thereof. Therefore, the embodiments described above should be construed as being exemplified and not limiting the present disclosure. The scope of the present disclosure should be understood that all changes or modifications derived from the definitions and scopes of the claims and their equivalents fall within the scope of the disclosure.

The invention claimed is:

1. A polynucleotide comprising a nucleotide sequence having at least 90% sequence identity to SEQ ID NO: 2, 3 or 4, wherein said polynucleotide comprises at least one of the following substitutions:

(i) the nucleotide adenine (A) at a position corresponding to position 27 of SEQ ID NO: 1 is substituted with thymine (T);

(ii) the nucleotide cytosine (C) at a position corresponding to position 28 of SEQ ID NO: 1 is substituted with guanine (G);

(iii) the nucleotide adenine (A) at a position corresponding to position 36 of SEQ ID NO: 1 is substituted with cytosine (C), and wherein said polynucleotide has promoter activity.

2. The polynucleotide of claim 1, wherein the nucleotides at positions corresponding to positions 66 and 261 of SEQ ID NO: 1 are further substituted with other nucleotides.

3. The polynucleotide of claim 1, wherein the nucleotide at a position corresponding to position 66 of SEQ ID NO: 1 is further substituted with another nucleotide.

4. The polynucleotide of claim 1, wherein the nucleotide adenine (A) at a position corresponding to position 27 of SEQ ID NO: 1 is substituted with thymine (T);

the nucleotide cytosine (C) at a position corresponding to position 28 of SEQ ID NO: 1 is substituted with guanine (G);

the nucleotide cytosine (C) at a position corresponding to position 31 of SEQ ID NO: 1 is substituted with guanine (G);

the nucleotide cytosine (C) at a position corresponding to position 32 of SEQ ID NO: 1 s substituted with thymine (T); and the nucleotide adenine (A) at a position corresponding to position 36 of SEQ ID NO: 1 is substituted with cytosine (C).

5. The polynucleotide of claim 4, wherein the polynucleotide comprises a nucleotide sequence having at least 95% sequence identity to SEQ ID NO: 2.

6. The polynucleotide of claim 4, wherein the polynucleotide comprises the nucleotide sequence of SEQ ID NO: 2.

7. The polynucleotide of claim 2, wherein the nucleotide adenine (A) at a position corresponding to position 27 of SEQ ID NO: 1 is substituted with thymine (T);

the nucleotide cytosine (C) at a position corresponding to position 28 of SEQ ID NO: 1 is substituted with guanine (G);

the nucleotide cytosine (C) at a position corresponding to position 31 of SEQ ID NO: 1 is substituted with guanine (G);

the nucleotide cytosine (C) at a position corresponding to position 32 of SEQ ID NO: 1 is substituted with thymine (T);

the nucleotide adenine (A) at a position corresponding to position 36 of SEQ ID NO: 1 is substituted with cytosine (C);

the nucleotide cytosine (C) at a position corresponding to position 66 of SEQ ID NO: 1 is substituted with thymine (T); and the nucleotide adenine (A) at a position corresponding to position 261 of SEQ ID NO: 1 is substituted with guanine (G).

8. The polynucleotide of claim 7, wherein the polynucleotide comprises a nucleotide sequence having at least 95% sequence identity to SEQ ID NO: 3.

9. The polynucleotide of claim 7, wherein the polynucleotide comprises the nucleotide sequence of SEQ ID NO: 3.

10. The polynucleotide of claim 3, wherein the nucleotide adenine (A) at a position corresponding to position 27 of SEQ ID NO: 1 is substituted with thymine (T);

the nucleotide cytosine (C) at a position corresponding to position 28 of SEQ ID NO: 1 is substituted with guanine (G);

the nucleotide cytosine (C) at a position corresponding to position 31 of SEQ ID NO: 1 is substituted with guanine (G);

the nucleotide cytosine (C) at a position corresponding to position 32 of SEQ ID NO: 1 is substituted with thymine (T);

the nucleotide adenine (A) at a position corresponding to position 36 of SEQ ID NO: 1 is substituted with cytosine (C); and the nucleotide cytosine (C) at a position corresponding to position 66 of SEQ ID NO: 1 is substituted with thymine (T).

11. The polynucleotide of claim 10, wherein the polynucleotide comprises a nucleotide sequence having at least 95% sequence identity to SEQ ID NO: 4.

12. The polynucleotide of claim 10, wherein the polynucleotide comprises the nucleotide sequence of SEQ ID NO: 4.

13. The polynucleotide of claim 1, wherein the polynucleotide is operably linked to a gene encoding a target protein.

14. An expression cassette comprising:

the polynucleotide of claim 1; and a gene encoding a target protein and operably linked to the polynucleotide.

15. The expression cassette of claim 14, wherein the target protein comprises glutamate dehydrogenase (gdh).

16. A microorganism of the genus Corynebacterium, comprising the polynucleotide of claim 1.

17. The microorganism of claim 16, further comprising a gene encoding a target protein and operably linked to the polynucleotide.

18. The microorganism of claim 17, wherein the target protein comprises glutamate dehydrogenase (gdh).

19. The microorganism of claim 16, wherein the microorganism of the genus *Corynebacterium* is *Corynebacterium glutamicum.*

20. A method for producing a target substance, the method comprising:

culturing the microorganism of claim 16 in a medium; and recovering a target substance in the medium.

21. The method of claim 16, wherein the target substance comprises lysine, threonine, O-acetyl homoserine, or isoleucine.

* * * * *